United States Patent [19]

Crutcher et al.

[11] Patent Number: 5,167,873
[45] Date of Patent: Dec. 1, 1992

[54] BINARY SURFACTANT MIXTURES

[75] Inventors: Terry Crutcher; Jeffrey W. Perine; Joe D. Sauer; Kim R. Smith; James E. Borland, all of Baton Rouge, La.

[73] Assignee: Ethyl Corporation, Richmond, Va.

[21] Appl. No.: 788,817

[22] Filed: Nov. 7, 1991

[51] Int. Cl.$^5$ .............................................. C11D 1/18
[52] U.S. Cl. .................................... 252/546; 252/544; 252/548; 252/DIG. 5; 252/DIG. 13; 252/DIG. 14
[58] Field of Search ......... 252/544, 546, 548, DIG. 5, 252/DIG. 13, DIG. 14

[56] References Cited

U.S. PATENT DOCUMENTS

| | | | |
|---|---|---|---|
| 4,486,328 | 12/1984 | Knott et al. | 252/117 |
| 4,595,526 | 6/1986 | Lai | 252/545 |
| 4,938,953 | 7/1990 | Pena et al. | 252/DIG. 13 |

Primary Examiner—Patrick P. Garvin
Assistant Examiner—E. D. Irzinski
Attorney, Agent, or Firm—Patricia J. Hogan

[57] ABSTRACT

Surfactant mixtures which have foamability performance and/or cost advantages over the individual components consist of 50-95% by weight of an alkyldimethylbetaine in which the alkyl group contains 8-18 carbons and 50-5% by weight of a fatty acid alkanolamide. Preferred mixtures are those in which the betaine is tetradecyldimethylbetaine and the alkanolamide is cocodiethanolsuperamide.

5 Claims, No Drawings

BINARY SURFACTANT MIXTURES

FIELD OF INVENTION

This invention relates to surfactant compositions and more particularly to such compositions which are mixtures of betaines and alkanolamides.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal or better performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. Thus, e.g., a mixture of (A) a more costly surfactant which provides good foamability by itself with (B) a less expensive surfactant which provides poorer foamability by itself will provide an intermediate foamability.

SUMMARY OF INVENTION

It has been found that a mixture of 50-95% by weight of an alkyldimethylbetaine in which the alkyl group contains 8-18 carbons and 50-5% by weight of a fatty acid alkanolamide provides foamability performance and/or cost advantages over the individual components of the surfactant mixture.

DETAILED DESCRIPTION

Betaines which may be used in the practice of the invention are the alkyldimethylbetaines in which the alkyl group contains 8-18 carbons. A particularly preferred betaine is tetradecyldimethylbetaine.

Fatty acid alkanolamides which may be used in admixture with the betaines are the known nonionic surfactants usually designated as superamides, i.e., alkanolamides obtained by reacting a fatty acid, usually a fatty acid containing 8-18 carbons, with an alkanolamine in equimolar proportions. The preferred alkanolamide is cocodiethanolsuperamide.

The betaine/alkanolamide mixtures of the invention are synergistic, i.e., provide foam levels higher than can be achieved by the use of either component alone, whenever they contain 50-95% by weight of the betaine. They are also more cost effective than the betaine component alone, and some of them are even more cost effective than the alkanolamide alone. Optimum foamability is obtained when the mixtures have a betaine content of 70-80% by weight, while the mixtures containing 50-55% by weight of the betaine component are most cost effective.

The invention is advantageous in that it provides novel surfactant mixtures which can provide acceptable levels of foam more economically than the individual components of the mixtures. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Dissolve varying amounts of tetradecyldimethylbetaine and cocodiethanolsuperamide in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1-3 twice and (5) calculating the average of the three measurements. The proportions of betaine and alkanolamide used in preparing each of the solutions and the foam heights obtained from them are shown in the table below.

TABLE

| % Betaine | % Alkanolamide | Foam Height (mL) |
| --- | --- | --- |
| 100 | 0 | 33 |
| 90 | 10 | 34 |
| 85 | 15 | 35 |
| 75 | 25 | 36 |
| 65 | 35 | 35 |
| 50 | 50 | 34 |
| 40 | 60 | 26 |
| 25 | 75 | 13 |
| 0 | 100 | 17 |

What is claimed is:

1. A surfactant mixture consisting of 50-95% by weight of an alkyldimethylbetaine in which the alkyl group contains 8-18 carbons and 50-5% by weight of a fatty acid alkanolamide.

2. The surfactant mixture of claim 1 wherein the alkanolamide contains an alkyl group of 8-18 carbons.

3. The surfactant mixture of claim 2 wherein the alkyldimethylbetaine is tetradecyldimethylbetaine and the alkanolamide is cocodiethanolsuperamide.

4. The surfactant mixture of claim 1 containing about 70-80% by weight of the betaine.

5. The surfactant mixture of claim 1 containing about 50-55% by weight of the betaine.

* * * * *